(12) United States Patent
Maehara

(10) Patent No.: US 12,085,455 B2
(45) Date of Patent: Sep. 10, 2024

(54) MEASUREMENT DEVICE AND MEASUREMENT SYSTEM

(71) Applicant: SONY SEMICONDUCTOR SOLUTIONS CORPORATION, Kanagawa (JP)

(72) Inventor: Masataka Maehara, Kanagawa (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 790 days.

(21) Appl. No.: 17/250,520

(22) PCT Filed: Aug. 6, 2019

(86) PCT No.: PCT/JP2019/030911
§ 371 (c)(1),
(2) Date: Jan. 31, 2021

(87) PCT Pub. No.: WO2020/032028
PCT Pub. Date: Feb. 13, 2020

(65) Prior Publication Data
US 2021/0293628 A1    Sep. 23, 2021

(30) Foreign Application Priority Data

Aug. 8, 2018 (JP) ................................. 2018-149347

(51) Int. Cl.
*G01K 7/01* (2006.01)
*B01L 3/00* (2006.01)
(Continued)

(52) U.S. Cl.
CPC ............ *G01K 7/01* (2013.01); *B01L 3/50851* (2013.01); *B01L 7/04* (2013.01); *G01K 13/12* (2013.01);
(Continued)

(58) Field of Classification Search
CPC ........ G05D 23/00; G05D 23/19; G05D 23/27; G05D 23/20; B01L 3/50851; B01L 7/04;
(Continued)

(56) References Cited

U.S. PATENT DOCUMENTS 5,981,268 A   11/1999   Kovacs et al.
6,051,422 A    4/2000   Kovacs et al.
(Continued)

FOREIGN PATENT DOCUMENTS

CN     1284166 A      2/2001
EP     1040345 A1    10/2000
(Continued)

OTHER PUBLICATIONS

EPO machine-generated English language translation Ogi et al. WO 2017061171 A1, patented Apr. 13, 2017 (Year: 2017).*
(Continued)

*Primary Examiner* — Alexander S Noguerola
(74) *Attorney, Agent, or Firm* — CHIP LAW GROUP

(57) ABSTRACT

In a device that measures biopotentials of cells in a solution, the solution is controlled at a constant temperature. A measurement device includes a substrate, a sensing control circuit, a temperature sensor, a front surface side heat radiating unit, a back surface side heat radiating unit, and a temperature control unit. A plurality of electrodes each detecting a potential in the solution is arranged on the front surface of the substrate. The sensing control circuit is arranged on the substrate and controls detection of potentials at the plurality of electrodes. The temperature sensor is arranged on the substrate and detects a temperature of the solution. The front surface side heat radiating unit is arranged on the front surface side of the substrate and radiates heat. The back surface side heat radiating unit is arranged on the back surface side that is a surface different (Continued)

from the front surface of the substrate, and radiates heat. The temperature control unit controls the temperature of the solution on the basis of the temperature detected by the temperature sensor.

19 Claims, 9 Drawing Sheets

(51) Int. Cl.
*B01L 7/00* (2006.01)
*B01L 7/04* (2010.01)
*G01K 13/12* (2006.01)
*G01N 27/327* (2006.01)
*G01N 33/487* (2006.01)
*G05D 23/00* (2006.01)
*G05D 23/19* (2006.01)
*G05D 23/20* (2006.01)
*H10N 10/10* (2023.01)

(52) U.S. Cl.
CPC ....... *G01N 33/48742* (2013.01); *G05D 23/00* (2013.01); *G05D 23/19* (2013.01); *G05D 23/1927* (2013.01); *G05D 23/20* (2013.01); *H10N 10/10* (2023.02)

(58) Field of Classification Search
CPC .. B01L 2300/18–1894; G01N 33/4836; G01N 33/48742
See application file for complete search history.

(56) References Cited

U.S. PATENT DOCUMENTS

| RE37,977 | E | 2/2003 | Sugihara et al. |
| 2005/0161192 | A1* | 7/2005 | Shigeura ................... B01L 7/52 |
| | | | 62/62 |
| 2006/0057771 | A1* | 3/2006 | Kovacs .............. G01N 33/4836 |
| | | | 438/106 |
| 2009/0258412 | A1 | 10/2009 | Moriwaki et al. |
| 2016/0245788 | A1* | 8/2016 | Wang ................. G01N 33/4836 |

FOREIGN PATENT DOCUMENTS

| EP | 1710017 A1 * | 10/2006 | ............... B01L 7/00 |
| JP | 11-187865 A | 7/1999 | |
| JP | 2002-523726 A | 7/2002 | |
| JP | 2006-177921 A | 7/2006 | |
| JP | 2008-062209 A | 3/2008 | |
| JP | 2008-151595 A | 7/2008 | |
| JP | 2008-286690 A | 11/2008 | |
| JP | 2009-254260 A | 11/2009 | |
| JP | 2015-059929 A | 3/2015 | |
| JP | 2018-072130 A | 5/2018 | |
| WO | 1998/054294 A1 | 12/1998 | |
| WO | 1999/034202 A1 | 7/1999 | |
| WO | WO 2004024330 A2 * | 3/2004 | ............... B01L 7/00 |
| WO | 2013/153667 A1 | 10/2013 | |
| WO | 2015/040930 A1 | 3/2015 | |
| WO | WO 2015054245 A1 * | 4/2015 | .............. C12M 1/34 |
| WO | WO 2017061171 A1 * | 4/2017 | .......... G01N 27/416 |
| WO | 2019/073774 A1 | 4/2019 | |

OTHER PUBLICATIONS

International Search Report and Written Opinion of PCT Application No. PCT/JP2019/030911, issued on Nov. 5, 2019, 13 pages of ISRWO.

* cited by examiner

MEASUREMENT DEVICE AND MEASUREMENT SYSTEM

CROSS REFERENCE TO RELATED APPLICATIONS

This application is a U.S. National Phase of International Patent Application No. PCT/JP2019/030911 filed on Aug. 6, 2019, which claims priority benefit of Japanese Patent Application No. JP 2018-149347 filed in the Japan Patent Office on Aug. 8, 2018. Each of the above-referenced applications is hereby incorporated herein by reference in its entirety.

TECHNICAL FIELD

The present disclosure relates to a measurement device and a measurement system. More specifically, the present disclosure relates to a measurement device that measures biopotentials of cells in a culture solution and a measurement system using the measurement device.

BACKGROUND ART

It is conventionally known that activity of nerve cells or the like can be measured by measuring a change in potential near the cells while culturing the nerve cells or the like in a culture solution. An ion concentration of a cell membrane changes with the activity of the nerve cells. This change is measured as a change in potential. As such a measurement system, a system is used including a signal processing means in which a substrate including a plurality of electrodes each detecting a cell potential is arranged at the bottom of a cylindrical resin frame that stores a culture solution, and the cell potential detected by the electrodes is processed (for example, see Patent Document 1).

CITATION LIST

Patent Document

Patent Document 1: Japanese Patent Application Laid-Open No. 08-062209

SUMMARY OF THE INVENTION

Problems to be Solved by the Invention

In the conventional technology described above, there is a problem that temperature of the culture solution fluctuates. In a case where a large number of electrodes for potential detection are arranged to detect a cell potential, it is necessary to process the detected cell potential at high speed. There is a problem that a high-speed processing circuit generates a large amount of heat, and the temperature of the culture solution rises due to heat transfer, which affects the activity of cells.

The present disclosure has been made in view of the problems described above, and an object of the present disclosure is to control a solution at a constant temperature in a device that measures biopotentials of cells in the solution.

Solutions to Problems

The present disclosure has been made to solve the problems described above, and a first aspect thereof is a measurement device including: a substrate on which a plurality of electrodes each detecting a potential in a solution is arranged on a front surface; a sensing control circuit that is arranged on the substrate and controls detection of potentials at the plurality of electrodes; a temperature sensor that is arranged on the substrate and detects a temperature of the solution; a front surface side heat radiating unit that is arranged on a front surface side of the substrate and radiates heat; a back surface side heat radiating unit that is arranged on a back surface side that is a surface different from the front surface of the substrate and radiates heat; and a temperature control unit that controls the temperature of the solution on the basis of the temperature detected by the temperature sensor.

Furthermore, in the first aspect, a reservoir unit that stores the solution may be further included.

Furthermore, in the first aspect, a temperature adjustment unit that performs adjustment of the temperature of the solution may be further included, and the temperature control unit may control the temperature of the solution by controlling temperature adjustment in the temperature adjustment unit.

Furthermore, in the first aspect, the temperature adjustment unit may perform the temperature adjustment via either the front surface side heat radiating unit or the back surface side heat radiating unit.

Furthermore, in the first aspect, the temperature adjustment unit may perform the temperature adjustment by a Peltier element.

Furthermore, in the first aspect, the temperature adjustment unit may further include a cooling unit that performs cooling of the Peltier element.

Furthermore, in the first aspect, the cooling unit may perform the cooling by circulating cooling water.

Furthermore, in the first aspect, the front surface side heat radiating unit may include metal.

Furthermore, in the first aspect, the front surface side heat radiating unit may be connected to a ground line that supplies a ground potential that serves as a reference for the sensing control circuit.

Furthermore, in the first aspect, the back surface side heat radiating unit may include metal.

Furthermore, in the first aspect, the back surface side heat radiating unit may be connected to a ground line that supplies a ground potential that serves as a reference for the sensing control circuit.

Furthermore, in the first aspect, a shielding unit that performs shielding from unnecessary radiation from the temperature adjustment unit may be further included.

Furthermore, in the first aspect, the shielding unit may be connected to a ground line.

Furthermore, in the first aspect, the shielding unit may be connected to the ground line that supplies a ground potential that serves as a reference for the sensing control circuit.

Furthermore, in the first aspect, the sensing region may include a plurality of electrode cells arranged each including the electrode and an amplifier circuit that amplifies a biopotential detected by the electrode.

Furthermore, in the first aspect, a reference electrode that applies a reference potential that serves as a reference for the potential to the solution may be further included.

Furthermore, in the first aspect, a plurality of the temperature sensors may be arranged on the substrate, and the temperature control unit may control the temperature of the solution on the basis of temperatures detected by the plurality of temperature sensors.

Furthermore, in the first aspect, a second temperature sensor may be further included that is arranged at a position different from that of the substrate and detects the temperature of the solution, and the temperature control unit may control the temperature of the solution on the basis of temperatures detected by the temperature sensor and the second temperature sensor.

Furthermore, a second aspect of the present disclosure is a measurement system including: a substrate on which a plurality of electrodes each detecting a potential in a solution is arranged on a front surface; a sensing control circuit that is arranged on the substrate and controls detection of potentials at the plurality of electrodes; a temperature sensor that is arranged on the substrate and detects a temperature of the solution; a front surface side heat radiating unit that is arranged on a front surface side of the substrate and radiates heat; a back surface side heat radiating unit that is arranged on a back surface side that is a surface different from the front surface of the substrate and radiates heat; a temperature control unit that controls the temperature of the solution on the basis of the temperature detected by the temperature sensor; and a processing circuit that processes the detected biopotential.

In such aspects, there is an effect that while heat is radiated, by the front surface side heat radiating unit and the back surface side heat radiating unit, from the substrate on which the sensing control circuit that controls detection of potential of the solution, the temperature of the solution is detected by the temperature sensor arranged in the vicinity of the electrode that detects the potential, and controlled.

Effects of the Invention

According to the present disclosure, in a device that measures biopotentials of cells in a solution, an excellent effect is obtained that the solution is controlled at a constant temperature.

MODE FOR CARRYING OUT THE INVENTION

Figure 1:
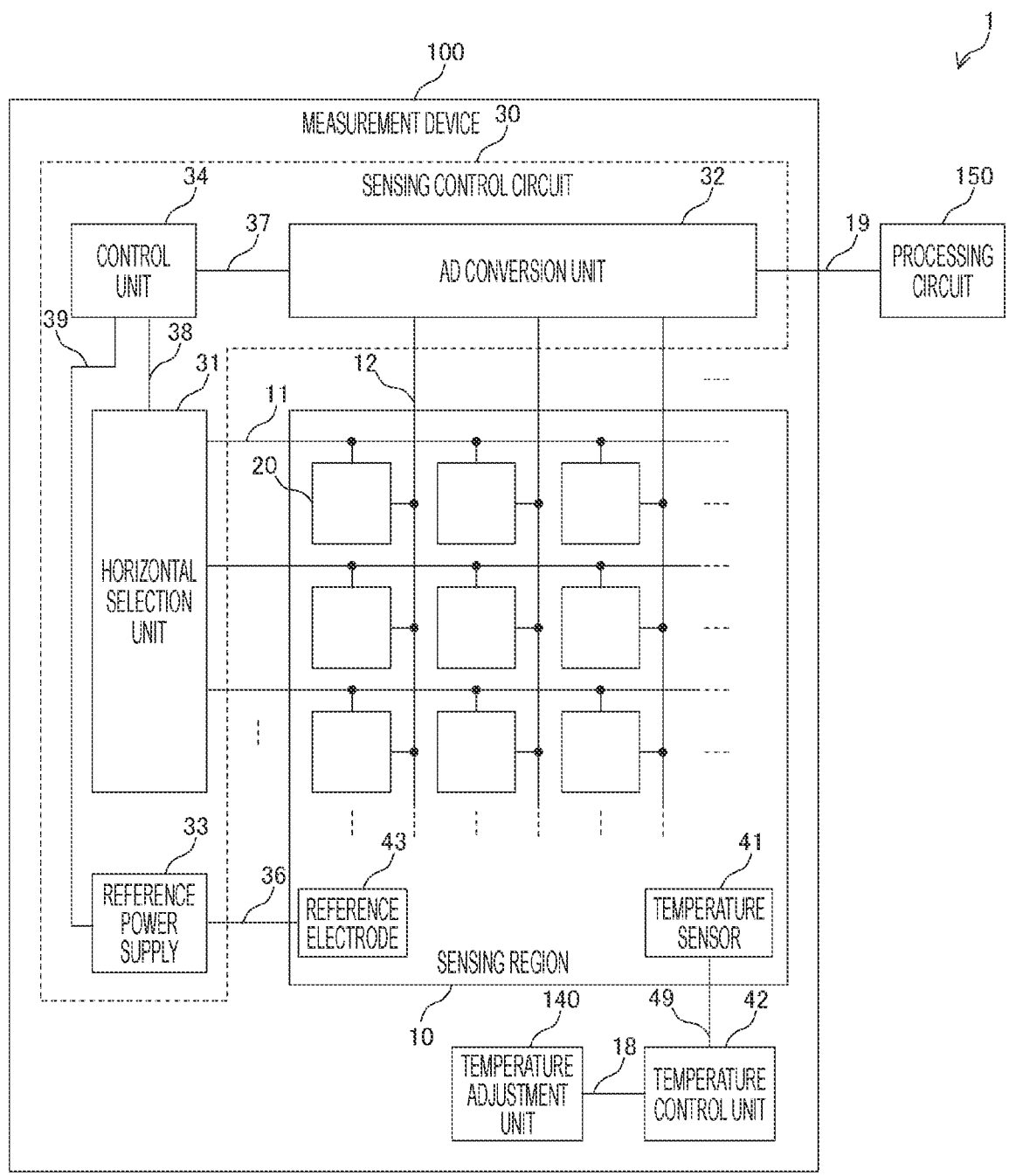
FIG. 1 is a diagram illustrating a configuration example of a measurement system according to an embodiment of the present disclosure.

Next, a mode for carrying out the present disclosure (hereinafter, referred to as an embodiment) will be described with reference to the drawings. In the drawings below, the same or similar portions are denoted by the same or similar reference numerals. However, the drawings are schematic, and dimensional ratios and the like of respective portions do not always match actual ones. Furthermore, it goes without saying that portions are included where dimensional relationships and ratios are different between the drawings. Furthermore, embodiments will be described in the following order.

1. First Embodiment
2. Second Embodiment
3. Third Embodiment

1. First Embodiment

[Configuration of Measurement System]

FIG. 1 is a diagram illustrating a configuration example of a measurement system according to an embodiment of the present disclosure. The figure is a block diagram illustrating a configuration example of a measurement system 1. The measurement system 1 in the figure includes a measurement device 100 and a processing circuit 150.

The measurement device 100 is a measurement device that measures potentials of biological cells or the like in a solution. The measurement device 100 measures potentials of biological cells such as nerve cells cultured in a culture solution stored in a reservoir unit 104 described later. In biological cells such as nerve cells and cardiomyocytes, the ion concentration near the cell membrane changes locally with activity. By detecting this local change in ion concentration as a change in potential, it is possible to observe the activity of nerve cells or the like.

The measurement device 100 in the figure includes a sensing region 10, a sensing control circuit 30, a reference electrode 43, a temperature sensor 41, a temperature control unit 42, and a temperature adjustment unit 140.

The sensing region 10 is a region in which a biopotential is detected. The sensing region 10 is formed on a front surface of a semiconductor substrate 50 described later. As illustrated in the figure, electrode cells 20, the reference electrode 43, and the temperature sensor 41 are arranged in the sensing region 10.

Each of the electrode cells 20 detects a local biopotential. The electrode cell 20 includes an electrode that detects the biopotential, performs detection of the biopotential on the basis of control by the sensing control circuit 30, and outputs a signal depending on the detected biopotential. The electrode cells 20 are arranged in a two-dimensional lattice in the sensing region 10 in the figure. Furthermore, in the sensing region 10, signal lines 11 and 12 are arranged in an XY matrix. Each of the signal lines 11 is a signal line that transmits a control signal that controls the detection of the biopotential in the electrode cell 20, is arranged for each row of the sensing region 10, and is wired commonly to the electrode cells 20 arranged in each row. Each of the signal lines 12 is a signal line that transmits an output signal depending on the biopotential detected by the electrode cell 20, is arranged in each column of the sensing region 10, and is wired commonly to the electrode cells 20 arranged in each column. Details of a configuration of the electrode cell 20 will be described later. For example, the electrode cells 20 of 500 rows and 500 columns can be arranged in the sensing region 10.

The reference electrode 43 is an electrode that applies a reference potential that serves as a reference in detection of the biopotential to the solution.

The temperature sensor 41 is a sensor that is arranged on the surface of the semiconductor substrate 50 and detects a temperature of the solution. As described later, the temperature sensor 41 can be arranged on the same surface as a surface on which the electrode cells 20 are arranged on the semiconductor substrate 50. For the temperature sensor 41, for example, an electronic circuit can be used including an electrode constituting a resistance temperature detector and a transistor that supplies a constant current to the electrode. The electrode includes, for example, platinum. A terminal voltage of the electrode can be output via a signal line 49 as the temperature detected by the temperature sensor 41.

The sensing control circuit 30 includes a horizontal selection unit 31, an analog-to-digital (AD) conversion unit 32, a reference power supply 33, and a control unit 34. The sensing control circuit 30 can be arranged on the semiconductor substrate 50.

The horizontal selection unit 31 generates the control signal for the electrode cell 20. The horizontal selection unit 31 applies the control signal to the electrode cell 20 via the signal line 11. At this time, the horizontal selection unit 31 sequentially applies the control signal for each row of the electrode cells 20 arranged in the sensing region 10.

The AD conversion unit 32 performs analog-to-digital conversion on the output signal from the electrode cell 20, and outputs the converted output signal to the processing circuit 150. The AD conversion unit 32 can be configured such that an analog-to-digital converter is arranged for each signal line 12, for example. As a result, output signals of the electrode cells 20 arranged in the row of the sensing region 10 can be simultaneously subjected to analog-to-digital conversion, and a time required for analog-to-digital conversion can be shortened. Biopotentials simultaneously subjected to analog-to-digital conversion are sequentially transferred to the processing circuit 150 via a signal line 19.

The reference power supply 33 generates the reference potential and supplies the reference potential to the reference electrode 43. The reference power supply 33 supplies the reference potential via a signal line 36.

The temperature control unit 42 controls the temperature of the solution. The temperature control unit 42 controls the temperature of the solution on the basis of the temperature detected by the temperature sensor 41. For example, the temperature control unit 42 can perform feedback control. Specifically, a difference is calculated between a set temperature (for example, 37° C.) and the temperature detected by the temperature sensor 41, and on the basis of the difference, the temperature adjustment unit 140 described later is controlled to perform heating and cooling. As a result, the temperature of the solution can be controlled. The temperature control unit 42 in the figure calculates the difference described above on the basis of the terminal voltage of the temperature sensor 41 transmitted by the signal line 49, and outputs a control signal to the temperature adjustment unit 140 via a signal line 18, thereby performing control of the temperature of the solution.

The temperature adjustment unit 140 performs temperature adjustment of the solution on the basis of the control by the temperature control unit 42. The temperature adjustment unit 140 can perform the temperature adjustment by cooling or heating the solution. For example, a Peltier element can be used for the temperature adjustment unit 140.

The processing circuit 150 performs processing of the biopotential measured by the measurement device 100. For example, analysis processing of the activity of biological cells based on the measured biopotential, and the like correspond to the processing. For the processing circuit 150, for example, a circuit including a microprocessor can be used.

As described later, a front surface side heat radiating unit 103 and a back surface side heat radiating unit 132 are further arranged in the measurement device 100 in the figure. The front surface side heat radiating unit 103 and the back surface side heat radiating unit 132 radiate heat of the semiconductor substrate 50 in which the sensing region 10 and the sensing control circuit 30 are arranged. In a case where a large number of electrode cells 20 are arranged in the sensing region 10 as described above, it is necessary to perform detection of the biopotential at high speed in measurement of the activity of biological cells. Furthermore, the AD conversion unit 32 also needs to perform high-speed analog-to-digital conversion. Such a high-speed circuit generates a large amount of heat, and the temperature of the semiconductor substrate 50 rises. For this reason, the solution is heated and affects the activity of biological cells. Thus, the front surface side heat radiating unit 103 and the back surface side heat radiating unit 132 are arranged to radiate the heat of the semiconductor substrate 50, and the temperature rise is prevented. Note that, the temperature adjustment unit 140 performs temperature adjustment via the back surface side heat radiating unit 132.

[Configuration of Electrode Cell]

Figure 2:
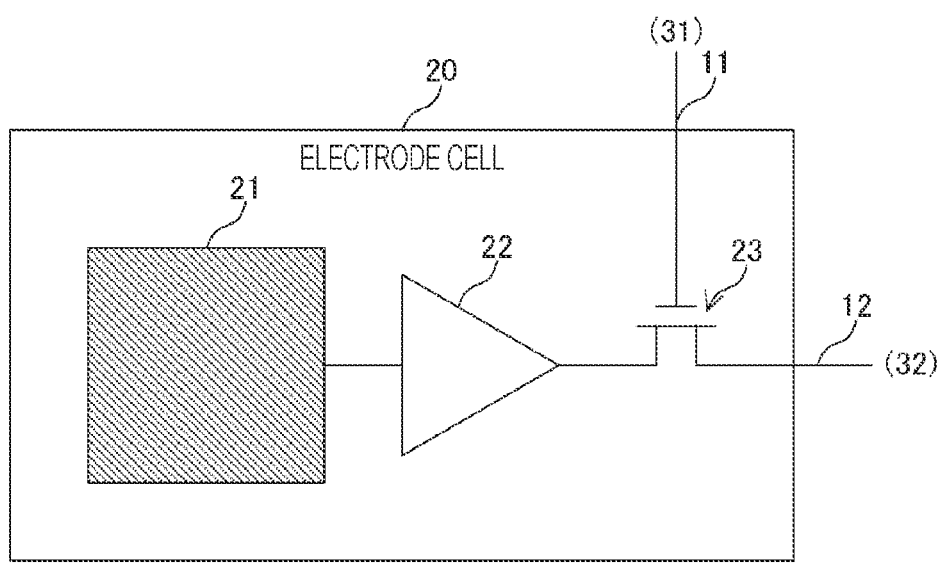
FIG. 2 is a diagram illustrating a configuration example of an electrode cell according to the embodiment of the present disclosure.

FIG. 2 is a diagram illustrating a configuration example of the electrode cell according to the embodiment of the present disclosure. The electrode cell 20 in the figure includes an electrode 21, an amplifier circuit 22, and a switch element 23.

The electrode 21 is an electrode that detects a biopotential. The electrode 21 is formed on the front surface of the semiconductor substrate 50 and is arranged adjacent to the solution. The electrode 21 can include, for example, a noble metal such as gold or platinum. Furthermore, the electrode 21 can also include a metal such as copper on which a film of these noble metals is formed. Since such noble metals are less eluted in solution, the biopotential can be measured without an influence on the activity of cells.

The amplifier circuit 22 is a circuit that amplifies the biopotential detected by the electrode 21. Since the biopotential detected by the electrode 21 is a feeble signal, amplification by the amplifier circuit 22 is performed. The input of the amplifier circuit 22 is connected to the electrode 21, and the output is connected to the switch element 23.

The switch element 23 is a switch that outputs the biopotential amplified by the amplifier circuit 22 to the signal line 12. The switch element 23 is arranged between the amplifier circuit 22 and the signal line 12, and includes a control terminal. The control terminal is connected to the signal line 11, and the control signal generated by the horizontal selection unit 31 is input. When the control signal is input to the control terminal, the switch element 23 conductively connects the output of the amplifier circuit 22 and the signal line 12 together. As a result, the amplified biopotential is output from the electrode cell 20.

The electrode 21 described above is exposed on the front surface of the semiconductor substrate 50. This is for contact with the solution. On the other hand, the amplifier circuit 22 and the switch element 23 are covered with a film of an insulator such as silicon oxide. This is for protection from the solutions and the like.

[Measurement Device]

Figure 3:
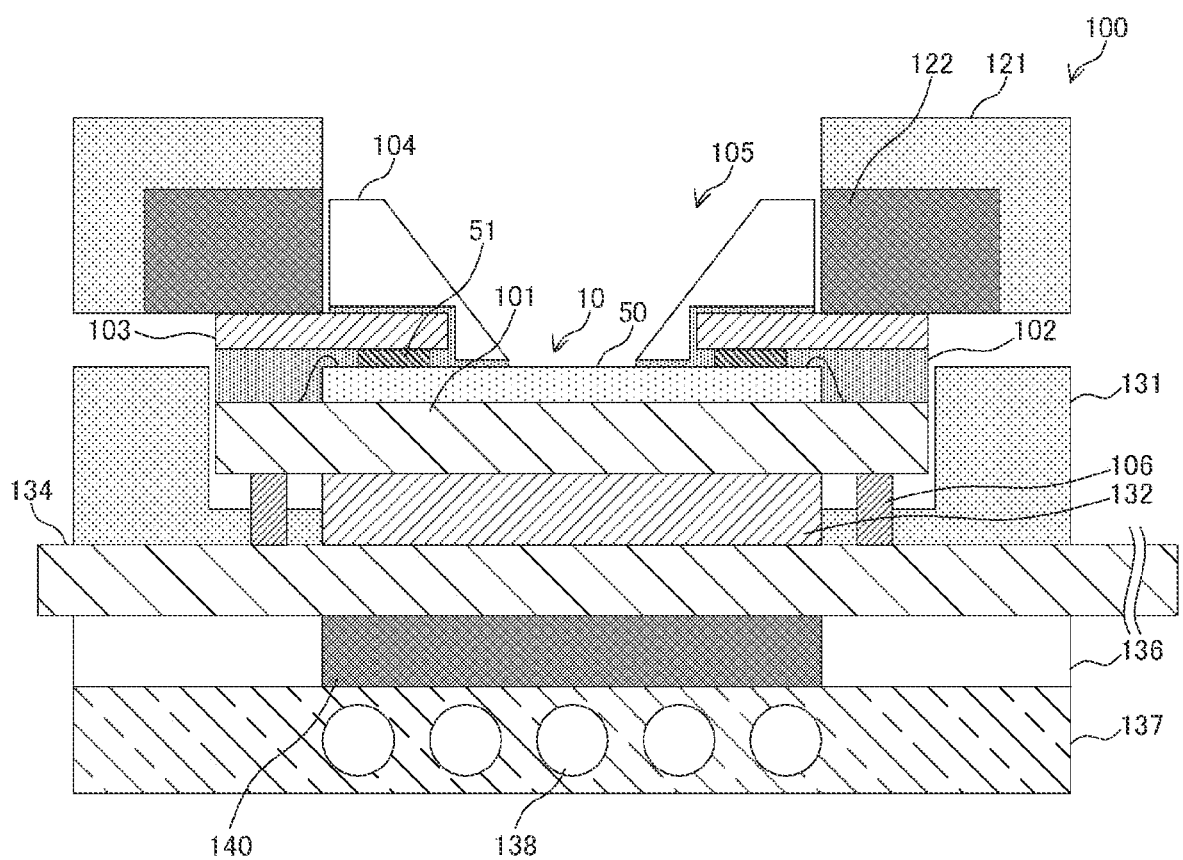
FIG. 3 is a sectional view illustrating a configuration example of a measurement device according to the embodiment of the present disclosure.

FIG. 3 is a sectional view illustrating a configuration example of the measurement device according to the embodiment of the present disclosure. The measurement device 100 in the figure includes the semiconductor substrate 50, an auxiliary chip 51, substrates 101 and 134, a sealing resin 102, the front surface side heat radiating unit 103, the reservoir unit 104, a connector 106, holding units 121 and 131, and a heat sink 122. Furthermore, the measurement device 100 in the figure further includes the back surface side heat radiating unit 132, a base plate 136, the temperature adjustment unit 140, a heat exhaust plate 137, and a cooling unit 138.

The semiconductor substrate 50 is a semiconductor substrate on which the sensing region 10, the sensing control circuit 30, and the temperature control unit 42 described in FIG. 1 are formed. The semiconductor substrate 50 can include a chip of a semiconductor such as silicon.

The auxiliary chip 51 is a semiconductor chip arranged on the front surface of the semiconductor substrate 50. The auxiliary chip 51 is formed with a part of the sensing control circuit 30 described above, and is flip-chip mounted and arranged on the front surface of the semiconductor substrate 50. For example, the AD conversion unit 32 can be arranged on the auxiliary chip 51.

The substrate 101 is a substrate on which the semiconductor substrate 50 is mounted. The substrate 101 can include, for example, a glass epoxy substrate. The semiconductor substrate 50 is bonded to the substrate 101 with an adhesive (not illustrated) and connected to a pad (not illustrated) formed on the substrate 101 by a bonding wire.

The front surface side heat radiating unit 103 is arranged on the front surface side of the semiconductor substrate 50 and radiates the heat of the semiconductor substrate 50. The front surface side heat radiating unit 103 in the figure is arranged adjacent to the auxiliary chip 51. The heat generated in the semiconductor substrate 50 is transferred to the front surface side heat radiating unit 103 via the auxiliary chip 51 and radiated. Note that, it is preferable to arrange a circuit having high power consumption such as the AD conversion unit 32 on the auxiliary chip 51. This is because the front surface side heat radiating unit 103 is arranged adjacently, whereby a heat radiating path is shortened. The front surface side heat radiating unit 103 can include, for example, a metal such as copper.

The reservoir unit 104 stores the solution. A mortar-shaped opening 105 is formed in the reservoir unit 104, and the solution is stored in the opening 105. The sensing region 10 of the semiconductor substrate 50 is arranged at the bottom of the opening 105. As a result, the sensing region 10 is adjacent to the solution. The reservoir unit 104 can include, for example, a resin such as polystyrene or Teflon (registered trademark), or glass.

The sealing resin 102 is a resin that seals the semiconductor substrate 50 and the auxiliary chip 51. Furthermore, the sealing resin 102 bonds the front surface side heat radiating unit 103 and the reservoir unit 104 to the semiconductor substrate 50. For the sealing resin 102, for example, an epoxy resin can be used.

The heat sink 122 is arranged adjacent to the front surface side heat radiating unit 103 and cools the front surface side heat radiating unit 103. The heat sink 122 in the figure is embedded in the holding unit 121, and cools the front surface side heat radiating unit 103 by transferring heat of the front surface side heat radiating unit 103 to the holding unit 121. Note that, the configuration of the heat sink 122 is not limited to this example. For example, a configuration can be used in which a heat radiation fin is arranged.

The back surface side heat radiating unit 132 is arranged on the back surface side of the semiconductor substrate 50 and radiates the heat of the semiconductor substrate 50. The back surface side heat radiating unit 132 in the figure is arranged adjacent to the substrate 101. The heat generated in the semiconductor substrate 50 is transferred to the back surface side heat radiating unit 132 via the substrate 101 and radiated. The back surface side heat radiating unit 132 can include, for example, a metal such as copper.

The holding units 121 and 131 hold the substrate 101, the semiconductor substrate 50 and the front surface side heat radiating unit 103 arranged on the substrate 101, the reservoir unit 104, and the like. The holding units 121 and 131 are arranged above and below the substrate 101 and the like, respectively, and hold the substrate 101 and the like by sandwiching them. Furthermore, the holding unit 131 is arranged on the front surface of the substrate 134. The substrate 101 and the reservoir unit 104 are held on the front surface of the substrate 134 by the holding units 121 and 131. The holding units 121 and 131 can include, for example, metal or resin.

The substrate 134 is a substrate on which the measurement system 1 is arranged. The substrate 134 can include a glass epoxy substrate similarly to the substrate 101. The processing circuit 150 (not illustrated) described in FIG. 1 is further arranged on the substrate 134. The substrates 101 and 134 can be electrically connected together by the connector 106.

The temperature adjustment unit 140 controls the temperature of the solution. The temperature adjustment unit 140 includes, for example, a Peltier element, and controls the temperature of the adjacent solution by performing cooling of the semiconductor substrate 50. The temperature adjustment unit 140 in the figure is arranged on the back surface side of the semiconductor substrate 50, and cools the semiconductor substrate 50 via the back surface side heat radiating unit 132 and the substrate 134. The Peltier element is an element including a semiconductor, and absorbs heat or radiates heat when a voltage is applied and a current flows between terminals. In the figure, heat is absorbed from a surface adjacent to the substrate 134, and is radiated from the other surface. By cooling the surface from which heat is radiated, it is possible to perform heat transfer from the substrate 134. Note that, the temperature adjustment unit 140 can also heat the semiconductor substrate 50. By reversing the direction of the current flowing through the Peltier element, it is possible to reverse the surface from which heat is absorbed and the surface from which heat is radiated, and heat the substrate 134 side.

The cooling unit 138 cools the temperature adjustment unit 140. The cooling unit 138 can include, for example, a plurality of pipes through which cooling water is circulated.

The base plate 136 holds the temperature adjusting unit 140. The heat exhaust plate 137 holds the cooling unit 138.

As illustrated in the figure, the semiconductor substrate 50 is sandwiched by the front surface side heat radiating unit 103 and the back surface side heat radiating unit 132, and heat is radiated from the front surface side and the back surface side simultaneously. As a result, heat radiation efficiency of the semiconductor substrate 50 can be improved.

Figure 4:
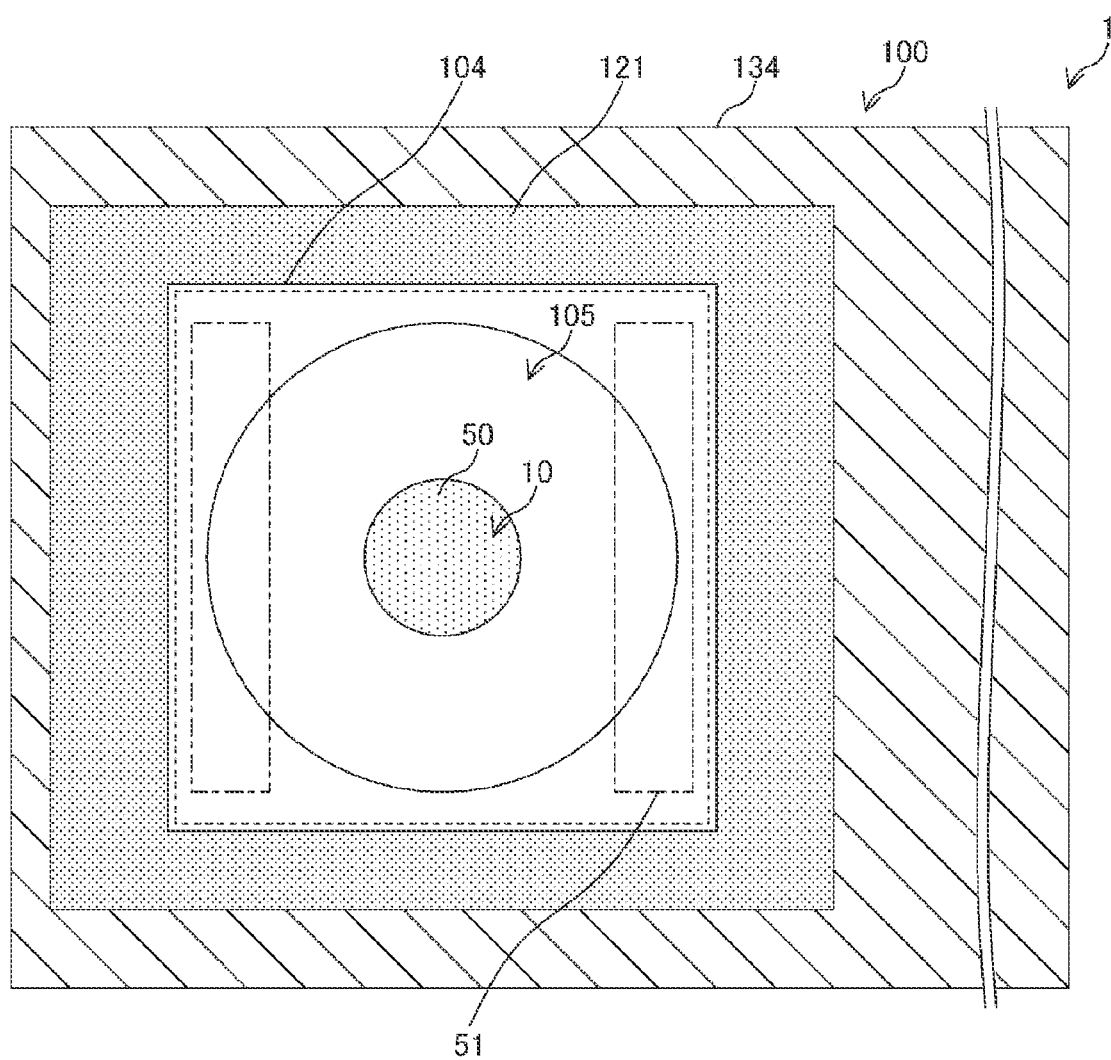
FIG. 4 is a plan view illustrating a configuration example of the measurement device according to the embodiment of the present disclosure.

FIG. 4 is a plan view illustrating a configuration example of the measurement device according to the embodiment of the present disclosure. The figure is a diagram illustrating an arrangement of the reservoir unit 104 and the like in the measurement device 100. In the figure, a dotted line rectangle represents the semiconductor substrate 50, and a chain line rectangle represents the auxiliary chip 51. As illustrated in the figure, the sensing region 10 of the semiconductor substrate 50 is arranged at the bottom of the mortar-shaped opening 105 of the reservoir unit 104.

Note that, the configuration of the semiconductor substrate 50 is not limited to this example. For example, a configuration can be used in which the auxiliary chip 51 is not arranged, and the sensing region 10, the sensing control circuit 30, the control unit 34, and the temperature control unit 42 described in FIG. 1 are arranged on one semiconductor substrate 50. In this case, the front surface side heat radiating unit 103 can be arranged adjacent to the front surface of the semiconductor substrate 50.

[Arrangement of Sensing Region]

Figure 5:
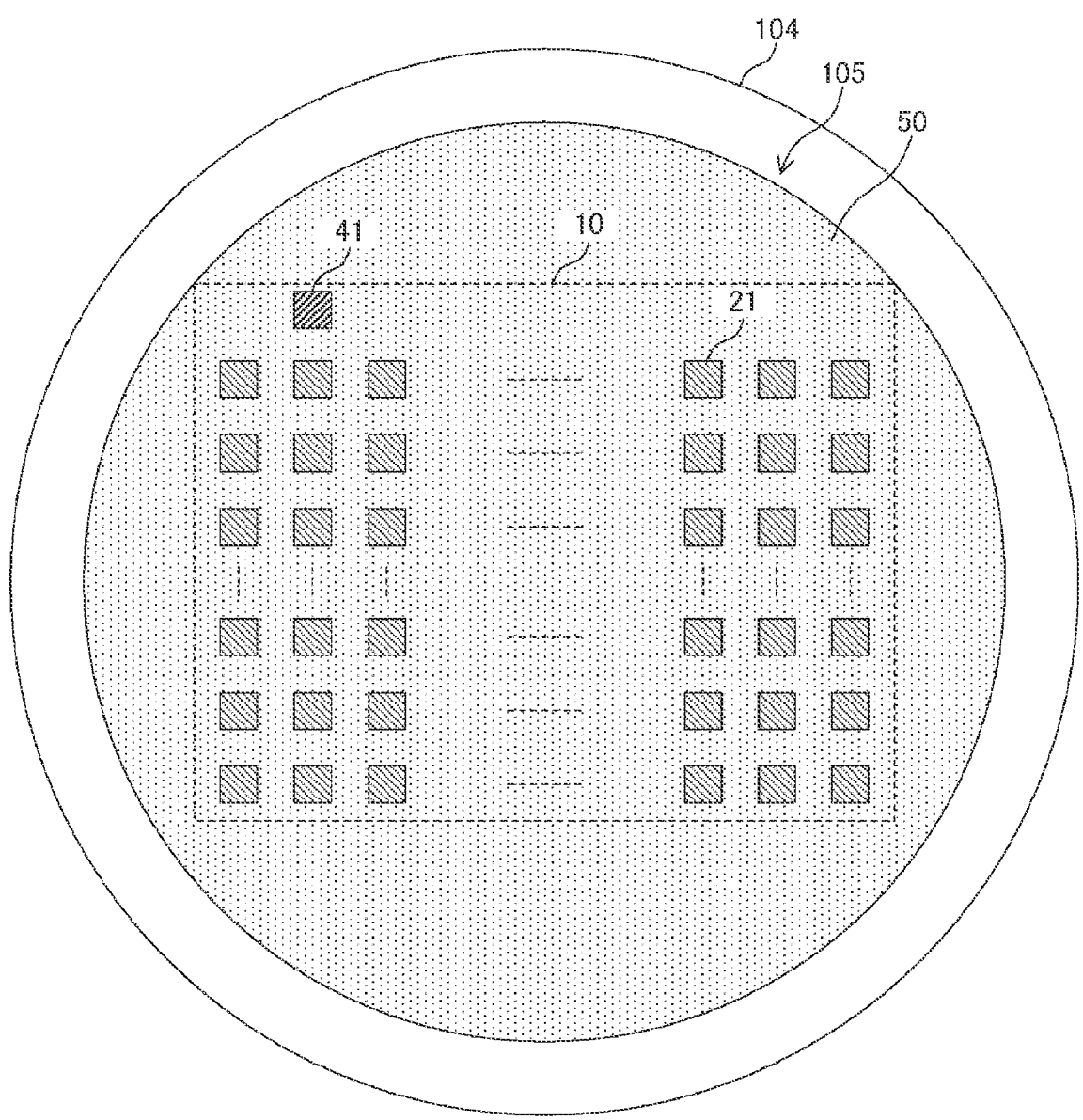
FIG. 5 is a diagram illustrating a configuration example of a sensing region according to a first embodiment of the present disclosure.

FIG. 5 is a diagram illustrating a configuration example of the sensing region according to the first embodiment of the present disclosure. The figure is a schematic diagram illustrating a configuration example of the sensing region 10 arranged at the bottom of the opening 105 of the reservoir unit 104. The electrodes 21 and the temperature sensor 41 are illustrated in the sensing region 10 in the figure. As illustrated in the figure, the electrodes 21 are arranged in a two-dimensional lattice. The temperature sensor 41 is arranged in the vicinity of the plurality of electrodes 21 arranged. As a result, the temperature of the solution in the vicinity of the electrode 21 can be precisely measured.

Configuration Example of Measurement Device

Figure 6:
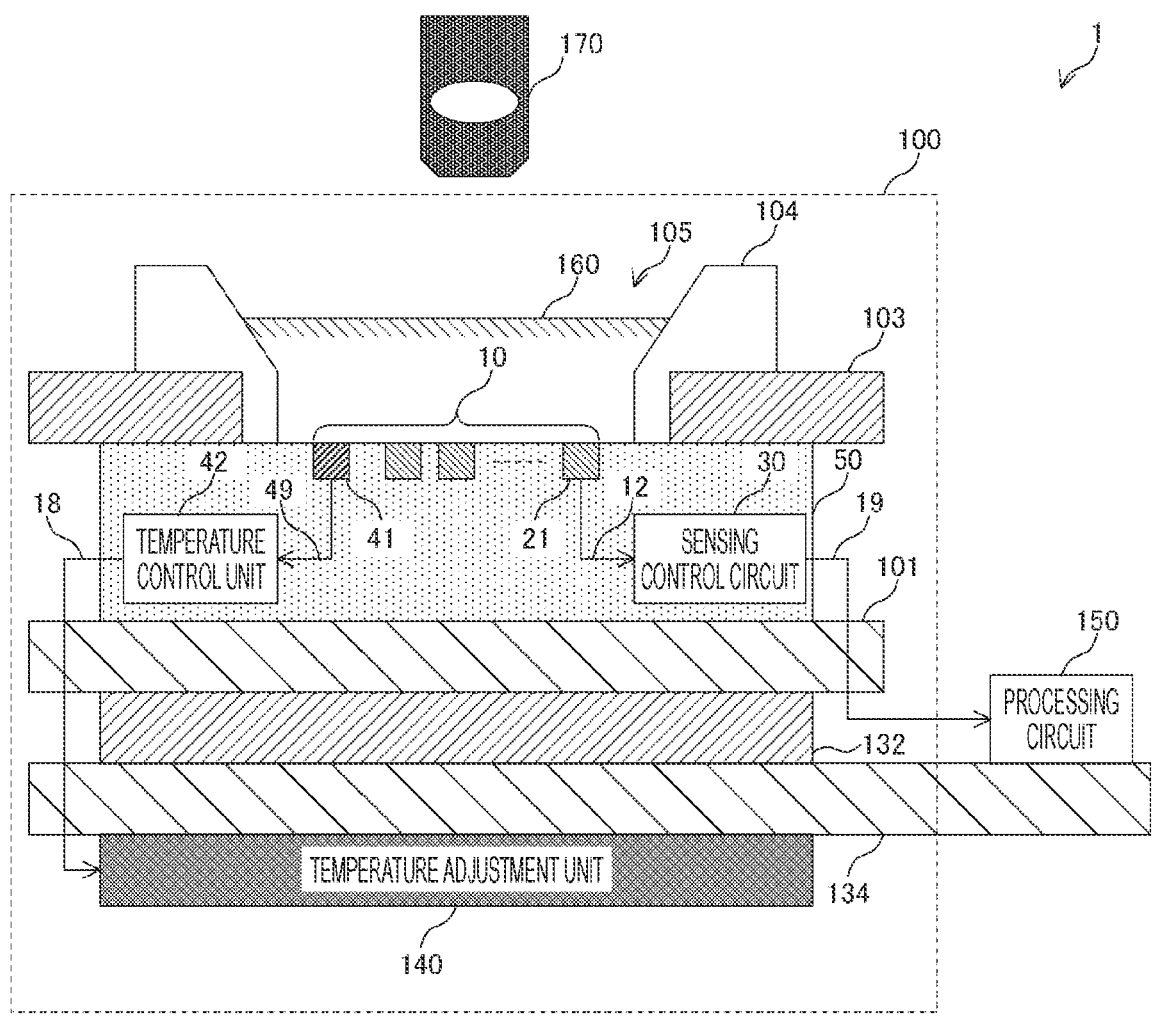
FIG. 6 is a diagram illustrating a configuration example of the measurement device according to the first embodiment of the present disclosure.

FIG. 6 is a diagram illustrating a configuration example of the measurement device according to the first embodiment of the present disclosure. The figure is a diagram schematically illustrating a configuration example of the measurement system 1 and the measurement device 100, and is a diagram in which other constituent elements and signal lines described in FIG. 1 are added to the sectional view of the measurement device 100 described in FIG. 3. For convenience, illustration of the reference electrode 43 and the elements other than the electrode 21 in the electrode cell 20, and illustration of the base plate 136 and the heat exhaust plate 137 are omitted.

The temperature sensor 41 and the plurality of electrodes 21 are arranged in the sensing region 10 on the front surface of the semiconductor substrate 50. A concave structure reservoir container is formed in which the front surface of the semiconductor substrate 50 is the bottom surface and the opening 105 of the reservoir unit 104 is the side wall. A solution 160 is stored in the reservoir container. For the solution 160, for example, an electrolytic solution or a cell culture solution can be used. The electrodes 21 are arranged in contact with the solution 160 and detect biopotentials of cells placed in the sensing region 10 on the basis of the control by the sensing control circuit 30. The detected biopotentials are subjected to analog-to digital conversion by the sensing control circuit 30, and processed by the processing circuit 150. On the other hand, the temperature sensor 41 performs detection of a temperature of the solution 160 and inputs the detected temperature to the temperature control unit 42. The temperature control unit 42 controls the temperature adjustment in the temperature adjustment unit 140 while comparing the temperature detected by the temperature sensor with the set temperature. Specifically, the temperature control unit 42 controls the current flowing through the Peltier element constituting the temperature adjustment unit 140 to control the cooling and the heating by the temperature adjustment unit 140. As a result, the solution 160 can be controlled at a constant temperature.

The sensing control circuit 30 and the temperature control unit 42 are arranged on the semiconductor substrate 50, whereby the measurement device 100 can be downsized. However, since the sensing control circuit 30 operates at high speed, the power consumption is high, and the amount of heat generation is large. For this reason, the temperature of the solution 160 rises. Thus, the front surface side heat radiating unit 103 and the back surface side heat radiating unit 132 are arranged, and heat is radiated from both surfaces of the semiconductor substrate 50. As a result, the heat radiation efficiency of the semiconductor substrate 50 can be improved. As described above, in a case where the semiconductor substrate 50 itself serves as a heat source, the temperature adjustment unit 140 can be configured to perform only the cooling. Furthermore, the figure illustrates an example in which a microscope 170 is arranged for observing a state of the cells. It is possible to perform measurement of the biopotentials while acquiring an image of the cells with the microscope, and possible to perform processing in the processing circuit 150. Note that, the semiconductor substrate 50 is an example of the substrate described in the claims.

The sensing region 10 and the temperature sensor 41 is arranged on the front surface of the semiconductor substrate 50 in this way, whereby the temperature of the solution 160 can be directly detected in the vicinity of the region where the biopotentials are detected, and accuracy of detection of the temperature of the solution 160 can be improved. Furthermore, it is possible to downsize the measurement device 100 by arranging and integrating the temperature control unit 42 and the temperature adjustment unit 140 under the reservoir unit 104.

Note that, the configuration of the measurement device 100 of the first embodiment of the present disclosure is not limited to this example. For example, a configuration can be used in which the temperature control unit 42 is arranged on the substrate 134. Furthermore, an air cooling fan can also be used as the temperature adjustment unit 140. The temperature adjustment unit 140 can be arranged also on the front surface side heat radiating unit 103 side. It is also possible to use a configuration in which two temperature adjustment units are arranged for both the front surface side heat radiating unit 103 and the back surface side heat radiating unit 132.

As described above, the measurement device 100 of the first embodiment of the present disclosure includes the temperature sensor 41 arranged on the semiconductor substrate 50 on which biopotential detection electrodes are arranged, to control the temperature of the solution 160, and the front surface side heat radiating unit 103 and the back surface side heat radiating unit 132 arranged. As a result, the heat radiation efficiency of the semiconductor substrate 50 can be improved, and the temperature of the solution 160 can be controlled to be constant.

2. Second Embodiment

The measurement device 100 of the first embodiment described above detects the temperature of the solution 160 by one temperature sensor 41. On the other hand, the measurement device 100 of the second embodiment of the present disclosure is different from the first embodiment described above in that the temperature is detected by a plurality of sensors.

[Configuration of Measurement Device]

Figure 7:
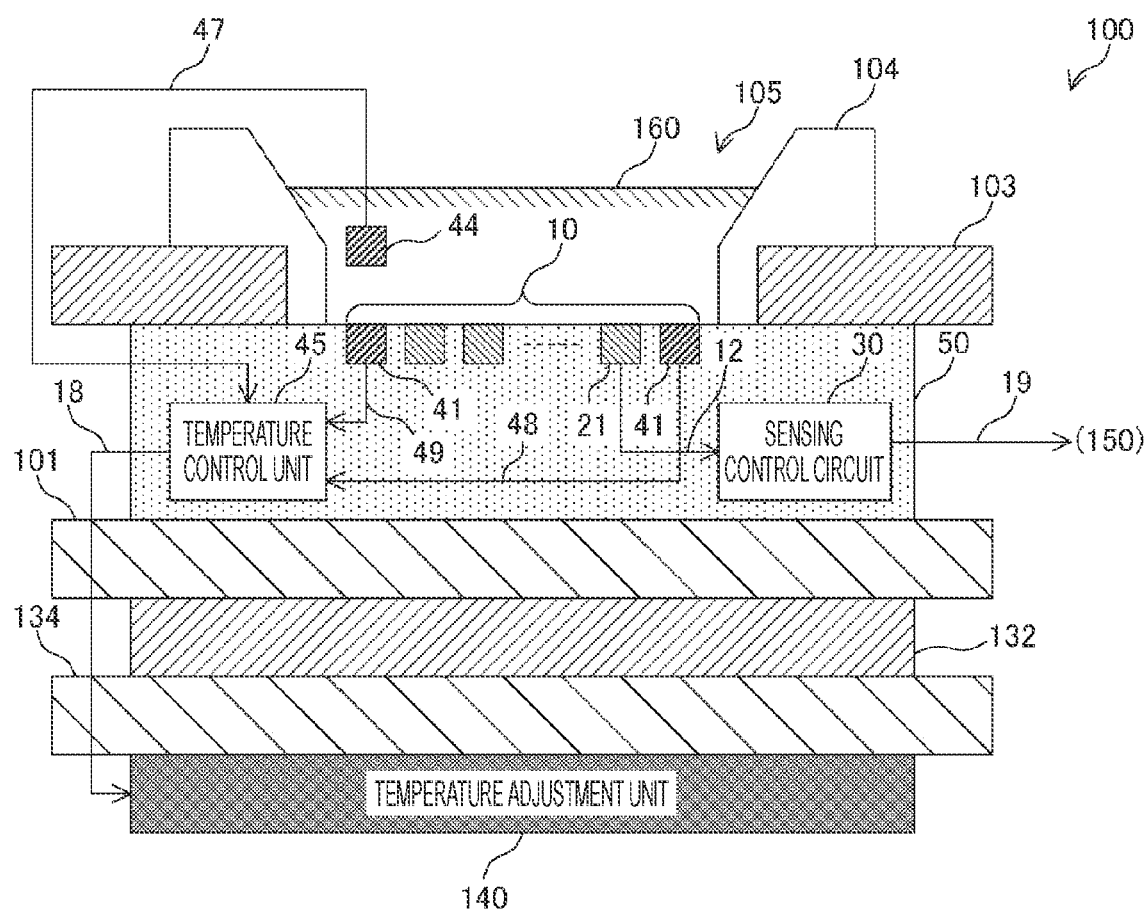
FIG. 7 is a diagram illustrating a configuration example of a measurement device according to a second embodiment of the present disclosure.

FIG. 7 is a diagram illustrating a configuration example of the measurement device according to the second embodiment of the present disclosure. The figure is different from the FIG. 6 described above in that the measurement device 100 includes a plurality of the temperature sensors 41 arranged on the semiconductor substrate 50, a temperature sensor 44 arranged at a position different from that of the semiconductor substrate 50 is further arranged, and a temperature control unit 45 is provided instead of the temperature control unit 42.

Two temperature sensors 41 are arranged in the sensing region 10 of the semiconductor substrate 50 in the figure. Furthermore, the temperature sensor 44 is suspended and arranged in the solution 160. For the temperature sensor 44, for example, a resistance temperature detector including a film of a metal such as platinum can be used separately from the temperature sensor 41. The added temperature sensor 41 and temperature sensor 44 are connected to the temperature control unit 45 by signal lines 48 and 47, respectively.

The temperature control unit 45 in the figure controls the temperature of the solution 160 on the basis of the temperatures detected by the temperature sensors 41 and 44. The temperature control unit 45 can perform temperature control on the basis of, for example, an average of the temperatures detected by the multiple temperature sensors 41 and 44. Furthermore, for example, it is possible to perform control so that the temperatures detected by the multiple temperature sensors 41 and 44 fall within a predetermined range. Note that, the temperature sensor 44 is an example of the second temperature sensor described in the claims.

[Arrangement of Sensing Region]

Figure 8:
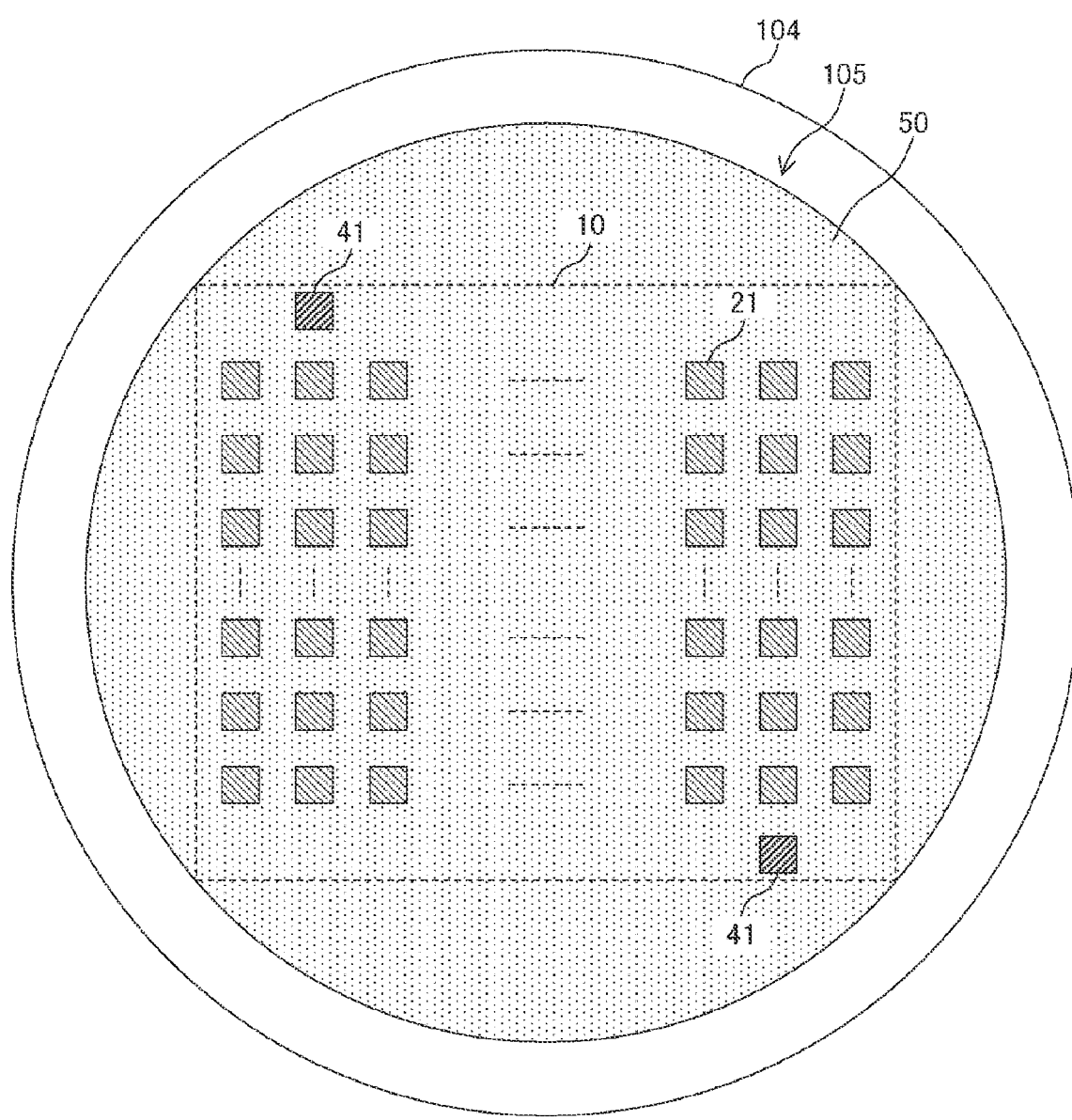
FIG. 8 is a diagram illustrating a configuration example of a sensing region according to the second embodiment of the present disclosure.

FIG. 8 is a diagram illustrating a configuration example of the sensing region according to the second embodiment of the present disclosure. As illustrated in the figure, the two temperature sensors 41 can be arranged diagonally in the sensing region 10.

The configuration of the measurement device 100 other than this is similar to the configuration of the measurement device 100 described in the first embodiment of the present disclosure, and thus the description thereof will be omitted.

As described above, since the measurement device 100 of the second embodiment of the present disclosure measures the temperature of the solution 160 by the multiple temperature sensors, the accuracy of detection of the temperature can be improved.

3. Third Embodiment

In the measurement device 100 of the first embodiment described above, the temperature adjustment unit 140 is arranged adjacent to the substrate 134. On the other hand, the measurement device 100 of the third embodiment of the present disclosure is different from the first embodiment described above in that a shielding unit is arranged between the temperature adjustment unit 140 and the substrate 134.

Configuration Example of Measurement Device

Figure 9:
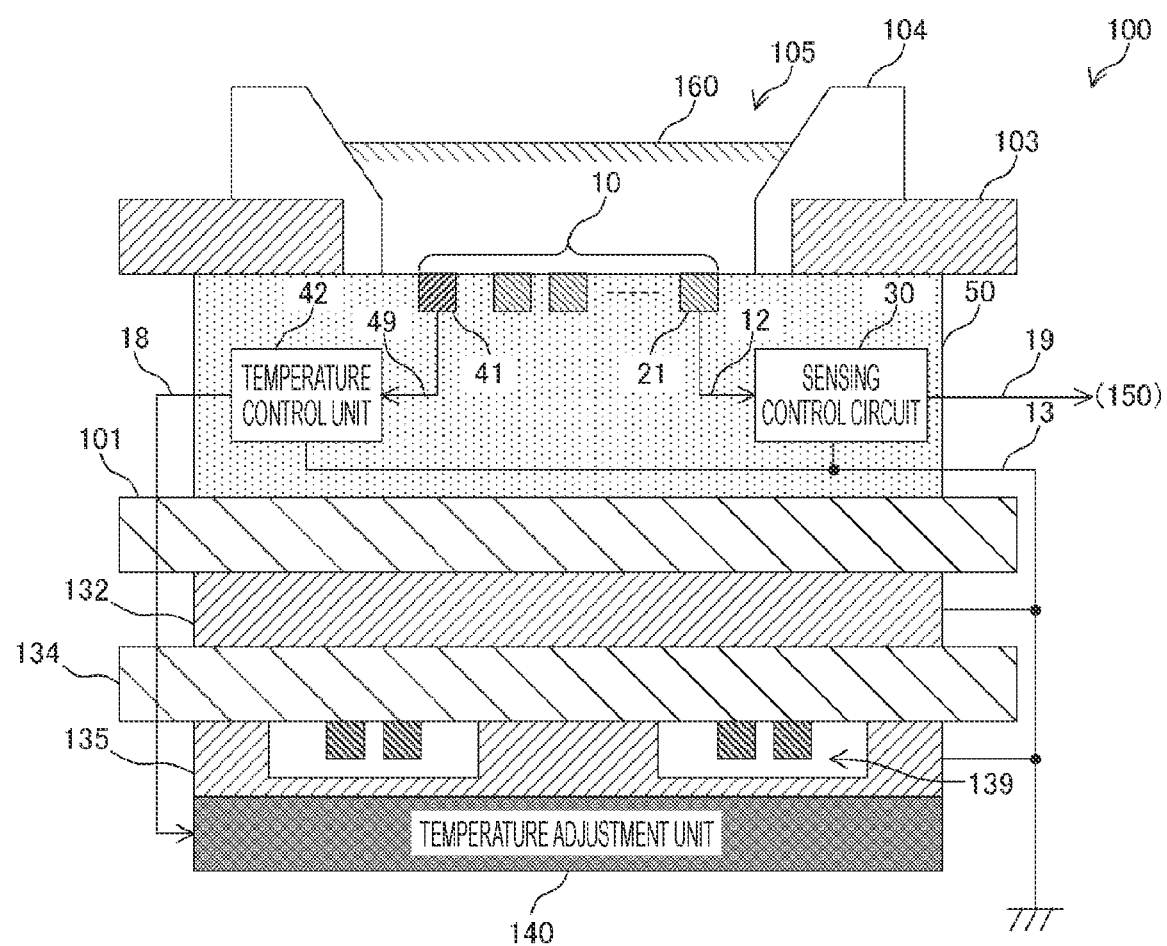
FIG. 9 is a diagram illustrating a configuration example of a measurement device according to a third embodiment of the present disclosure.

FIG. 9 is a diagram illustrating a configuration example of the measurement device according to the third embodiment of the present disclosure. The measurement device 100 in the figure is different from the measurement device 100 described in FIG. 6 in that a shielding unit 135 is arranged between the temperature adjustment unit 140 and the substrate 134, and the shielding unit 135 and the back surface side heat radiating unit 132 are grounded.

The shielding unit 135 transfers heat between the back surface side heat radiating unit 132, the substrate 134, and the temperature adjustment unit 140, and shields the temperature adjustment unit 140. The shielding unit 135 includes metal, and reduces an influence of unnecessary radiation of the temperature adjustment unit 140 on the sensing control circuit 30 and the like. The electrode cell 20 and the sensing control circuit 30 perform detection of a biopotential that is a feeble signal, and the like. On the other hand, a relatively large drive current flows through the Peltier element used in the temperature adjustment unit 140. When the unnecessary radiation due to the drive current for the Peltier element is mixed in the electrode cell 20 and the like, noise is generated, and an error occurs in the detected biopotential. Thus, the shielding unit 135 is arranged between the temperature adjustment unit 140 and the semiconductor substrate 50 to perform shielding from the unnecessary radiation. At this time, if the shielding unit 135 has an area larger than that of the semiconductor substrate 50, shielding effect can be improved.

Note that, in the shielding unit 135 in the figure, a recess is formed in a part of a surface adjacent to the substrate 134. In the recess, an element 139 can be arranged for removing noise superimposed on a power supply line and the like.

A ground line 13 in the figure is a wiring line that supplies the ground potential of the sensing control circuit 30 and the temperature control unit 42. It is also possible to connect the shielding unit 135 to the ground line 13 to perform grounding. By grounding the shielding unit 135, it is possible to improve shielding ability. Furthermore, as illustrated in the figure, the back surface side heat radiating unit 132 can also be connected to the ground line 13, to be grounded. As a result, double shielding can be performed from the unnecessary radiation from the temperature adjustment unit 140.

Furthermore, the shielding unit 135 can be connected to a ground line (not illustrated) different from the ground line 13. The ground line 13 corresponds to signal grounding to which the sensing control circuit 30 and the like are connected. By separating the ground line 13 from the ground line to which the shielding unit 135 is connected, it is possible to reduce an influence of the unnecessary radiation on the sensing control circuit 30 and the like.

Note that, the shielding unit 135 can be used in a floating state without being connected to the ground line 13. In this case, the shielding unit 135 is grounded via a stray capacitance. Furthermore, a configuration can also be used in which the front surface side heat radiating unit 103 is connected to the ground line 13.

The configuration of the measurement device 100 other than this is similar to the configuration of the measurement device 100 described in the first embodiment of the present disclosure, and thus the description thereof will be omitted.

As described above, the measurement device 100 according to the third embodiment of the present disclosure can reduce the noise of the biopotential by arranging the shielding unit 135 to perform shielding from the unnecessary radiation to the semiconductor substrate 50.

Lastly, the description of each of the embodiments described above is an example of the present disclosure, and the present disclosure is not limited to the embodiments described above. For this reason, it goes without saying that various changes other than the embodiments described above can be made depending on the design and the like as long as they do not deviate from the technical idea according to the present disclosure.

Note that, the present technology can also be configured as described below.

(1) A measurement device including:
a substrate on which a plurality of electrodes each detecting a potential in a solution is arranged on a front surface;
a sensing control circuit that is arranged on the substrate and controls detection of potentials at the plurality of electrodes;
a temperature sensor that is arranged on the substrate and detects a temperature of the solution;
a front surface side heat radiating unit that is arranged on a front surface side of the substrate and radiates heat;
a back surface side heat radiating unit that is arranged on a back surface side that is a surface different from the front surface of the substrate and radiates heat; and
a temperature control unit that controls the temperature of the solution on the basis of the temperature detected by the temperature sensor.

(2) The measurement device according to (1), further including a reservoir unit that stores the solution.

(3) The measurement device according to (1) or (2), further including
a temperature adjustment unit that performs adjustment of the temperature of the solution, in which
the temperature control unit controls the temperature of the solution by controlling temperature adjustment in the temperature adjustment unit.

(4) The measurement device according to (3), in which the temperature adjustment unit performs the temperature adjustment via either the front surface side heat radiating unit or the back surface side heat radiating unit.

(5) The measurement device according to (4), in which the temperature adjustment unit performs the temperature adjustment by a Peltier element.

(6) The measurement device according to (5), in which the temperature adjustment unit further includes a cooling unit that performs cooling of the Peltier element.

(7) The measurement device according to (6), in which the cooling unit performs the cooling by circulating cooling water.

(8) The measurement device according to any of (1) to (7), in which the front surface side heat radiating unit includes metal.

(9) The measurement device according to (8), in which the front surface side heat radiating unit is connected to a ground line that supplies a ground potential that serves as a reference for the sensing control circuit.

(10) The measurement device according to any of (1) to (7), in which the back surface side heat radiating unit includes metal.

(11) The measurement device according to (10), in which the back surface side heat radiating unit is connected to a ground line that supplies a ground potential that serves as a reference for the sensing control circuit.

(12) The measurement device according to any of (1) to (11), further including a shielding unit that performs shielding from unnecessary radiation from the temperature adjustment unit.

(13) The measurement device according to (12), in which the shielding unit is connected to a ground line.

(14) The measurement device according to (13), in which the shielding unit is connected to the ground line that supplies a ground potential that serves as a reference for the sensing control circuit.

(15) The measurement device according to any of (1) to (14), in which the sensing region includes a plurality of electrode cells arranged each including the electrode and an amplifier circuit that amplifies a biopotential detected by the electrode.

(16) The measurement device according to any of (1) to (15), further including a reference electrode that applies a reference potential that serves as a reference for the potential to the solution.

(17) The measurement device according to any of (1) to (16), in which
a plurality of the temperature sensors is arranged on the substrate, and
the temperature control unit controls the temperature of the solution on the basis of temperatures detected by the plurality of temperature sensors.

(18) The measurement device according to any of (1) to (17), further including
a second temperature sensor that is arranged at a position different from that of the substrate and detects the temperature of the solution, in which
the temperature control unit controls the temperature of the solution on the basis of temperatures detected by the temperature sensor and the second temperature sensor.

(19) A measurement system including:
a substrate on which a plurality of electrodes each detecting a potential in a solution is arranged on a front surface;
a sensing control circuit that is arranged on the substrate and controls detection of potentials at the plurality of electrodes;
a temperature sensor that is arranged on the substrate and detects a temperature of the solution;
a front surface side heat radiating unit that is arranged on a front surface side of the substrate and radiates heat;
a back surface side heat radiating unit that is arranged on a back surface side that is a surface different from the front surface of the substrate and radiates heat;
a temperature control unit that controls the temperature of the solution on the basis of the temperature detected by the temperature sensor; and
a processing circuit that processes the detected biopotential.

REFERENCE SIGNS LIST

1 Measurement system
10 Sensing region
13 Ground line
20 Electrode cell
21 Electrode
22 Amplifier circuit
23 Switch element
30 Sensing control circuit
31 Horizontal selection unit
32 AD conversion unit
33 Reference power supply
41, 44 Temperature sensor
42, 45 Temperature control unit
43 Reference electrode
50 Semiconductor substrate
100 Measurement device
101, 134 Substrate
103 Front surface side heat radiating unit
104 Reservoir unit
121, 131 Holding unit 122 Heat sink
132 Back surface side heat radiating unit
135 Shielding unit
138 Cooling unit
140 Temperature adjustment unit
150 Processing circuit
160 Solution
170 Microscope

The invention claimed is:

1. A measurement device, comprising:
a substrate;
a plurality of electrodes on a front surface of the substrate, wherein
each electrode of the plurality of electrodes is configured to detect a potential in a solution;
a sensing control circuit, on the substrate, configured to control the detection of the potential by each electrode of the plurality of electrodes;
a first temperature sensor, on the substrate, configured to detect a first temperature of the solution;
a front surface side heat radiating unit, on a front surface side of the substrate, wherein the front surface side heat radiating unit is configured to radiate heat of the substrate;
a back surface side heat radiating unit, on a back surface side of the substrate, wherein
the back surface side heat radiating unit is configured to radiate the heat, and
the back surface side of the substrate is different from the front surface of the substrate;
a temperature control unit configured to control a temperature of the solution based on the first temperature detected by the first temperature sensor;
a temperature adjustment unit configured to absorb the heat and radiate the heat to adjust the temperature of the solution based on the control by the temperature control unit; and
a shielding unit, between the temperature adjustment unit and the substrate, wherein the shielding unit is configured to shield at least one component of the measurement device from the heat radiation from the temperature adjustment unit.

2. The measurement device according to claim 1, further comprising a reservoir unit configured to store the solution.

3. The measurement device according to claim 1, wherein the temperature control unit is further configured to control the temperature of the solution based on the adjustment of the temperature the temperature adjustment unit.

4. The measurement device according to claim 3, wherein the temperature adjustment unit is further configured to adjust the temperature via at least one of the front surface side heat radiating unit or the back surface side heat radiating unit.

5. The measurement device according to claim 4, wherein the temperature adjustment unit includes a Peltier element, and
the temperature adjustment unit is further configured to adjust temperature by the Peltier element.

6. The measurement device according to claim 5, wherein the temperature adjustment unit further includes a cooling unit that is configured to cool the Peltier element.

7. The measurement device according to claim 6, wherein the cooling unit is further configured to cool the Peltier element based on circulation of cooling water.

8. The measurement device according to claim 1, wherein the front surface side heat radiating unit includes a metal.

9. The measurement device according to claim 8, wherein
the front surface side heat radiating unit is further configured to connect to a ground line that supplies a ground potential, and
the ground potential serves as a reference potential for the sensing control circuit for the detection of the potential.

10. The measurement device according to claim 1, wherein the back surface side heat radiating unit includes a metal.

11. The measurement device according to claim 10, wherein the back surface side heat radiating unit is further configured to connect to a ground line that supplies a ground potential, and
the ground potential serves as a reference potential for the sensing control circuit for the detection of the potential.

12. The measurement device according to claim 1, wherein the shielding unit is further configured to connect to a ground line.

13. The measurement device according to claim 12, wherein the ground line supplies a ground potential that serves as a reference potential for the sensing control circuit for the detection of the potential.

14. The measurement device according to claim 1, further comprising a sensing region which includes;
a plurality of electrode cells, wherein
each electrode cell of the plurality of the electrode cells includes an electrode of the plurality of electrodes; and
an amplifier circuit configured to amplify the potential detected by the electrode of the plurality of electrodes.

15. The measurement device according to claim 1, further comprising a reference electrode configured to apply a reference potential that serves as a reference for the potential to the solution.

16. The measurement device according to claim 1, further comprising:
a plurality of temperature sensors on the substrate, wherein the plurality of temperature sensors include the first temperature sensor,
the plurality of temperature sensors are configured to detect a plurality of temperatures of the solution respectively, and
the temperature control unit is further configured to control the temperature of the solution based on the plurality of temperatures detected by the plurality of temperature sensors.

17. The measurement device according to claim 1, further comprising:
a second temperature sensor at a specific position which is different from a position on the substrate, wherein
the second temperature sensor is configured to detect a second temperature of the solution, and
the temperature control unit is further configured to control the temperature of the solution based on the first temperature detected by the first temperature sensor and the second temperature detected by the second temperature sensor.

18. A measurement system, comprising:
a substrate;
a plurality of electrodes on a front surface of the substrate, wherein
each electrode of the plurality of electrodes is configured to detect a potential in a solution;
a sensing control circuit, on the substrate, wherein the sensing control circuit is configured to control the detection of the potential by each electrode of the plurality of electrodes;

a temperature sensor, arranged on the substrate, configured to detect a temperature of the solution;
a front surface side heat radiating unit, on a front surface side of the substrate, configured to radiate heat of the substrate;
a back surface side heat radiating unit, on a back surface side of the substrate, configured to radiate the heat, wherein the back surface side of the substrate is different from the front surface of the substrate;
a temperature control unit configured to control the temperature of the solution based on the temperature detected by the temperature sensor;
a temperature adjustment unit configured to absorb the heat and radiate the heat to adjust the temperature of the solution based on the control by the temperature control unit;
a shielding unit, between the temperature adjustment unit and the substrate, wherein the a shielding unit is configured to shield at least one component of the measurement system from the heat radiation from the temperature adjustment unit; and
a processing circuit that is configured to process the detected potential.

19. A measurement device, comprising:
a substrate;
a plurality of electrodes on a front surface of the substrate, wherein
each electrode of the plurality of electrodes is configured to detect a potential in a solution;
a sensing control circuit, on the substrate, configured to control the detection of the potential by each electrode of the plurality of electrodes;
a temperature sensor, on the substrate, configured to detect a temperature of the solution;
a front surface side heat radiating unit, on a front surface side of the substrate, configured to radiate heat of the substrate;
a back surface side heat radiating unit, on a back surface side of the substrate, wherein the back surface side heat radiating unit is configured to radiate the heat, wherein the back surface side of the substrate is different from the front surface of the substrate;
a temperature control unit configured to control the temperature of the solution based on the temperature detected by the temperature sensor;
a temperature adjustment unit configured to adjust the temperature of the solution based on the control by the temperature control unit; and
a shielding unit configured to shield at least one component of the measurement device from the heat radiation from the temperature adjustment unit, wherein the shielding unit is connected to a ground line.

* * * * *